US012023420B2

(12) United States Patent
Cognard et al.

(10) Patent No.: US 12,023,420 B2
(45) Date of Patent: Jul. 2, 2024

(54) VASCULAR STENT WITH ANTITHROMBOTIC PROPERTIES

(71) Applicants: UNIVERSITÉ PAUL SABATIER TOULOUSE III, Toulouse (FR); CENTRE HOSPITALIER UNIVERSITAIRE DE TOULOUSE, Toulouse (FR); CENTRE NATIONAL DE LA RECHERCHE SCIENTIFIQUE—CNRS, Paris (FR); INSERM-INSTITUT NATIONAL DE LA SANTÉ ET DE LA RECHERCHE MÉDICALE, Paris (FR)

(72) Inventors: Christophe Cognard, Toulouse (FR); Olivier Eichwald, Lauzerville (FR); Cédric Garcia, Labege (FR); Nofel Merbahi, Toulouse (FR); Bernard Payrastre, Tournefeuille (FR); Pierre Sie, Toulouse (FR); Aurélie Tokarski, Toulouse (FR); Ivan Vukasinovic, Belgrade (RS); Mohammed Yousfi, Saint-Orens-de-Gameville (FR)

(73) Assignees: UNIVERSITE PAUL SABATIER TOULOUSE III, Toulouse (FR); CENTRE HOSPITALIER UNIVERSITAIRE DE TOULOUSE, Toulouse (FI); CENTRE NATIONAL DE LA RECHERCHE SCIENTIFIQUE, Paris (FR); INSERM-INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 741 days.

(21) Appl. No.: 15/734,027

(22) PCT Filed: Jun. 5, 2019

(86) PCT No.: PCT/FR2019/051336
§ 371 (c)(1),
(2) Date: Dec. 1, 2020

(87) PCT Pub. No.: WO2019/234350
PCT Pub. Date: Dec. 12, 2019

(65) Prior Publication Data
US 2021/0213178 A1 Jul. 15, 2021

(30) Foreign Application Priority Data

Jun. 8, 2018 (FR) ........................... 1854996

(51) Int. Cl.
*A61L 31/10* (2006.01)
*A61L 31/02* (2006.01)
*A61L 31/04* (2006.01)

(52) U.S. Cl.
CPC ............. *A61L 31/10* (2013.01); *A61L 31/022* (2013.01); *A61L 31/047* (2013.01); *A61L 2420/02* (2013.01)

(58) Field of Classification Search
None
See application file for complete search history.

(56) References Cited

U.S. PATENT DOCUMENTS

| 4,283,469 | A | 8/1981 | Goebel | |
|---|---|---|---|---|
| 2007/0135906 | A1* | 6/2007 | Badylak | ............... A61M 29/02 623/1.44 |

FOREIGN PATENT DOCUMENTS

| WO | 9529647 A2 | 11/1995 |
|---|---|---|
| WO | 03045582 A1 | 6/2003 |
| WO | 2017004598 A1 | 1/2017 |

OTHER PUBLICATIONS

Liu, T., et al., Surface biomimetic modification with laminin-loaded heparin/poly-L-lysine nanoparticles for improving the biocompatibility, Materials Science and Engineering C 71 (2017) 929-936 (Year: 2017).*
International Search Report for corresponding application PCT/FR2019/051336 filed Jun. 5, 2019; dated Aug. 6, 2019.

* cited by examiner

*Primary Examiner* — H. Sarah Park
(74) *Attorney, Agent, or Firm* — CANTOR COLBURN LLP (57) ABSTRACT

The present invention relates to a vascular stent, deployed or non-deployed, the surface of which is coated by a film comprising at least one protein, to a process for coating of the surface of a vascular stent with a film comprising at least one protein and to a device for carrying out the process according to the invention.

15 Claims, 6 Drawing Sheets

VASCULAR STENT WITH ANTITHROMBOTIC PROPERTIES

TECHNICAL AREA

The present invention belongs to the field of medical devices and more particularly to that of vascular stents.

The invention relates to a vascular stent, deployed or non-deployed, the surface of which is coated by a film comprising at least one protein, to a process for coating of the surface of a vascular endoprosthesis with a film comprising at least one protein and to a device for carrying out the process according to the invention.

STATE OF THE ART

A vascular stent is a device most commonly made of metal, meshed and tubular that can be positioned in a human or animal cavity to dilate a stenosis or an occlusion and keep the cavity open. Vascular stents are mainly used in arteries, more rarely in veins.

Stents are mainly used in vascular pathologies (cardiology and endovascular neurosurgery) but can also be used in the urethra, trachea, oesophagus or bile ducts.

As the vascular stent is a foreign material to the human or animal body into which it is introduced, it is a device conducive to the formation of a clot or thrombus. When a vascular stent is placed, for example in an artery, this step must be followed by medication to prevent the formation of clots. This treatment is necessary for at least several weeks after the stent has been inserted until it is naturally covered by the cells of the inner wall of the artery. This process is called endothelialization.

Historically, drug treatment has been based on low-dose aspirin combined with ticlopidine (CAS no 55142-85-3). Today, this treatment has evolved and the drug combination includes aspirin and another anti-platelet agent such as clopidogrel (CAS no 113665-84-2), prasugrel (CAS no 150322-43-3) or ticagrelor (CAS no 274693-27-5).

There are two main types of vascular stents: so-called "bare" stents and "active" or pharmaco-active stents. Active stents are also called drug-eluting stents.

Active stents are generally distinguished from bare stents by the integration in a biodegradable polymer plated on the wire mesh of an antiproliferative substance that reduces the risk of delayed restenosis, due to the thickening of the vascular wall, by blocking the proliferation of smooth muscle cells in the vessel wall. This phenomenon is particularly critical in coronary pathology because the vessel treated by the stent is strongly reshaped by atherosclerosis and is highly inflammatory. Unfortunately, the substances diffused by the active stent, which are antimitotics, delay the endothelialization process, which is based on the multiplication of the circulating endothelial progenitors responsible for covering the stent. This leaves the active stent and the vessel wall in contact with it partially uncovered, which leads to a high risk of thrombosis in the treated area. The endothelialization of the stent mesh is thus incomplete and delayed and the formation of clots remains a potential danger justifying a strong anti-platelet treatment for a prolonged period of 3 to 12 months depending on the case in coronary pathology. Active stents are therefore not an ideal solution as they prolong the duration of the period at risk of thrombosis and impose treatment with a high systemic haemorrhagic risk for a long period of time.

Furthermore, active stents cannot be used in neurosurgery in the case of an ischaemic stroke or a ruptured aneurysm, as they would delay the healing of the vessel that has just been treated.

There is therefore a real need for vascular stents to overcome these defects, disadvantages and obstacles of the prior art, by preventing the activation of haemostasis, in particular of the platelets in contact with the stent without affecting the adhesion of the circulating endothelial progenitors which, by differentiating and multiplying, will lead to the restoration of the luminal endothelial cover in contact with the blood.

It is to the Applicants credit that they have developed a new type of vascular stent, overcoming both the previously mentioned defects and disadvantages of bare or active vascular stents.

The vascular stents according to the invention thus have several advantages over the vascular stents known in the state of the art and possess in particular antithrombotic properties, without having the disadvantage of limiting the endothelialization process, even partially. Once endothelialised, the wall and the stent become less thrombogenic and the anti-platelet therapy can be lightened, with fewer side effects.

The vascular stents according to the invention thus combine the advantages of bare and active stents, without having the disadvantages.

The vascular stents according to the invention may also possess antibacterial and/or anti-inflammatory properties.

The invention relates to a vascular stent, deployed or not deployed, whose surface is coated by a film comprising at least one protein of interest.

Advantageously, the at least one protein of interest comprised in the film was subjected to an electric field.

In the context of the invention, "proteins" or "proteins of interest" means proteins selected from the group comprising one or more blood plasma proteins (such as, for example, albumin, immunoglobulins (antibodies, essentially IgG), fibrinogen, alpha-1-antitrypsin, alpha-2 macroglobulin, transferrin, lipoproteins (essentially HDL and LDL)) and/or one or more synthetic biological macromolecules which, after the application of an electric field (e.g. pulsed), make it possible to obtain a film of at least one protein strongly adhered to the surface of the stent and having antithrombotic properties without preventing endothelialisation. Preferably, the at least one protein of interest may be albumin or a mixture of proteins from blood plasma, including albumin.

Advantageously, the at least one protein of interest is soluble at a pH between 3 and 12.

Advantageously, the film comprising the at least one protein of interest according to the invention, is a film of protein(s) (e.g. plasma) that can be deposited by applying an electric field (e.g. pulsed) on a solution comprising at least one protein of interest modified (e.g. destructured) or not by the application of the electric field. In contrast to a conventional deposition method without the application of an electric field, as for example described in WO2017/004598, the at least one protein of interest which has been subjected to the electric field coats the stent in a lasting way and with proven antithrombotic properties (see examples below).

Advantageously, the film comprising at least one protein of interest can be distributed homogeneously over the surface of the stent. The film comprising at least one protein of interest has a thickness which can vary according to the nature of the protein, the duration of exposure to the electric field and the nature of the said electric field. The thickness of the film comprising the at least one protein of interest may be greater than or equal to 30 Angstroms, and is preferably homogeneous over the surface of the stent. The protein concentration on the surface of the stent may be greater than or equal to 2 $\mu m^{-2}$.

Advantageously, the vascular stent according to the invention can be any commercially available bare vascular stent that has been subsequently treated to form a film of at least one protein of interest. It is a medical device, most often metallic, meshed and tubular, intended to be inserted into a natural human or animal cavity to keep it open. The vascular stent may be made of various materials such as metal alloys, silicone and polymers. Preferably, the vascular stent according to the invention is metallic and comprises one or more metallic alloy(s). For example, the metal alloy(s) may be selected from the group consisting of stainless steel, nickel/titanium (such as nitinol), tantalum, cobalt/chromium, platinum/chromium, alloys optionally including magnesium, and mixtures thereof.

Advantageously, the vascular stent according to the invention can be deployed or not deployed. Generally, the stent is non-deployed when it is stored in the original microcatheter (in which it is marketed), prior to implantation. The stent is said to be deployed when some or all of the stent is no longer in the microcatheter used to place it and the mesh of which it is made is partially or fully deployed outside of the original microcatheter. When a stent is deployed entirely in the open air (without constraints), it may have a diameter ranging from 2 mm to 60 mm depending on the type of stent, for example from 2 mm to 10 mm for a carotid stent, from 2 mm to 5 mm for an intracranial stent, from 18 mm to 46 mm for an aortic stent. A stent can be from 10 mm to 200 mm in length, e.g. 10 mm to 70 mm for a carotid stent, 10 mm to 35 mm for an intracranial stent, or up to 170 mm for an aortic stent.

Advantageously, the vascular stent according to the invention can be:
- a cardiac stent (often stiffer than an intracranial stent), either bare or comprising, for example, a biodegradable carrier such as salicylic acid, polylactic acid (PLLA) or magnesium. The vascular stent according to the invention may further comprise a polymer coating containing a drug and/or different materials (such as antibodies, carbon, etc.),
- a self-expanding cardiac stent or on an expandable balloon (pre-mounted on a balloon),
- a bare intracranial stent with a loose or dense mesh (Flow Diverter),
- a self-expanding intracranial, carotid or peripheral stent.

The vascular stent can for example be a stent for placement in the venous system (nitinol alloy; diameter 10-20 mm; length 40-160 mm) or an implant such as a cava filter (nitinol alloy, stainless steel or cobalt-chrome; diameter 25-40 mm; length up to 50 mm).

The antithrombotic properties of the vascular stents according to the invention can be observed for a prolonged period of time, ranging from one week to several months. For example, the antithrombotic properties may be observed for a period of more than or equal to 3 months, more than or equal to 6 months, or even more than or equal to 9 or 12 months.

The invention also relates to a process for coating the surface of a vascular stent, deployed or not deployed, with a film of at least one protein of interest, comprising the steps of:
- bringing the vascular stent into contact with an aqueous solution comprising at least one protein of interest,
- application of an electric field generated by a system of electrodes preferably comprising at least one first electrode, a dielectric and at least one second electrode, said dielectric electrically isolating the stent and the at least one second electrode from the at least one first electrode, and
- coating the surface of the stent with the film of at least one protein of interest.

Advantageously, the at least one first electrode is insulated from the stent by a dielectric. The dielectric insulates the at least one first electrode from the stent and the at least one second electrode. There is no electrical current flowing between the electrodes due to the presence of the dielectric (insulator). This results in the generation of an electric field (which can be pulsed) which will cause formation process of the film of at least one protein of interest.

Advantageously, during the implementation of the process according to the invention, the vascular stent can be deployed (or partially deployed, with part of the stent remaining embedded in the original duct or the microcatheter used to insert it). In deployed form, the surface is more accessible and facilitates the placement of the first electrode.

Advantageously, the aqueous solution comprises one or more proteins of interest as defined above. The concentration of protein(s) in the aqueous solution may be greater than or equal to 0.1 mg/ml. For example, when the protein is albumin, the concentration may be between 5 and 50 mg/ml when the aqueous solution is a buffered solution containing phosphate saline buffer (PBS) or between 30 and 50 mg/ml when the aqueous solution is blood plasma. The process according to the invention can be carried out in a solution containing one or more types of proteins. The aqueous solution comprising at least one protein may be for example blood plasma, a buffered solution comprising a buffer such as for example PBS (saline phosphate buffer) or saline distilled water (NaCl). The aqueous solution can thus be any aqueous solution that does not degrade the proteins of interest dissolved in it.

Advantageously, the aqueous solution containing at least one protein of interest can be animal or human blood plasma extracted directly from the patient (autologous transplant). This solution offers the advantage of treating the vascular stent just prior to implantation with a plasma that strongly limits the risks of patient rejection.

Advantageously, the pH of the aqueous solution comprising at least one protein of interest has a value such that the at least one protein is soluble during the implementation of the process. The aqueous solution is preferably homogeneous. The pH of the aqueous solution can thus be between 3 and 12, preferably between 6 and 9 and even more preferably between 7 and 8. The pH of the aqueous solution is, for example, 7.4.

The "isoelectric point" (IP) of a protein is the pH at which the overall electrical charge of the protein is neutral. At its Isoelectric Point, the protein has an equal number of positive and negative charges and there is no protein transport under an electric field. If the pH is higher than the IP then the overall charge of the protein is negative, otherwise it is positive. For example, the pH of human blood is regulated around 7.4 and albumin has a IP of 4.8, so the total charge of albumin in human blood is negative (7.4>4.8). Preferably, in the process according to the invention, the pH of the aqueous solution may be higher or lower than the IP of the protein(s) forming the film of at least one protein of interest.

Advantageously, when carrying out the process according to the invention, the aqueous solution comprising at least one protein of interest may be mobile or static, preferably static, with respect to the vascular stent. Preferably, the stent is immersed in the solution comprising at least one protein of interest, so that its entire surface can be coated by the protein film when carrying out the process.

Advantageously, the electric field is generated by a voltage signal applied to the system of electrodes. The electric field can thus be generated by energising the at least first electrode, which is insulated by the dielectric. The amplitude of the voltage signal can be in the range of 1 V to 50 kV. Preferably, the amplitude is in the range of 5 kV to 40 kV, and even more preferably in the range of 10 kV to 30 kV. The applied voltage can be positive and/or negative, preferably positive.

Advantageously, the voltage signal (and thus the resulting electric field) can have a periodic structure. It can be characterised by its period Tp (duration of the repeating pattern) and within a period by the duration Tv where the voltage is non-zero. The ratio Tv/Tp defines the duty cycle of the periodic signal. The repeating pattern in each period can be continuous by part (e.g. one pulse), sinusoidal, triangular or sawtooth-shaped. For example, the voltage signal is a pulse with a Tv duration of $5.10^{-7}$ s that repeats every 0.01 s (this is a continuous periodic signal with a frequency of 100 Hz and a duty cycle of $5.10^{-5}$). The frequency of the signal can thus have a value in the range 0.1 Hz to 100 kHz, preferably 1 Hz to 1 kHz, and the duty cycle a value in the range $5.10^{-8}$ to 1 (1 corresponds to a rectified or unrectified AC signal), preferably $5.10^{-6}$ to $5.10^{-3}$.

Advantageously, the electric field may be generated for a duration greater than or equal to 10 seconds, preferably greater than or equal to 5 minutes and even more preferably greater than or equal to 10 or 20 minutes. The duration may be increased or decreased depending on the type of protein, the protein concentration in the aqueous solution and/or the type of stent (e.g. material).

Advantageously, the voltage is applied to the at least one first electrode and the at least one second electrode is connected to earth. The voltage can also be applied to the at least one second electrode, with the at least one first electrode connected to earth. The stent can also be used as an electrode if it is metallic and separated from the second electrode by a dielectric.

Advantageously, the process according to the invention may be carried out in sterile or non-sterile conditions. The process can also include a sterilisation step. According to the invention, any sterilization method suitable for the sterilization of a vascular stent may be used. The sterilization step does not alter the antithrombotic properties of the vascular stent according to the invention.

Advantageously, when carrying out the procedure according to the invention, the stent is positioned in a receiving element, preferably tubular in shape. The process according to the invention may also include a heparinization step of the said receiving element.

The invention furthermore relates to a vascular stent obtainable by the process according to the invention.

The invention further relates to a device for carrying out the process according to the invention comprising:
  at least one first electrode,
  at least one second electrode,
  at least one dielectric isolating the first electrode from the second electrode,
  a receiving element that may contain the stent, preferably in the form of a dielectric tube (e.g. PVC).

Advantageously, the device for carrying out the process of the invention comprises a receiving element of tubular shape intended to receive the vascular stent, said receiving element preferably having a shape adapted to the shape of the vascular stent, preferably cylindrical, comprising an inlet for the aqueous solution comprising at least one protein and an outlet, said device being provided with an system of electrodes comprising at least one first electrode, a dielectric and at least one second electrode as well as a source of electrical energy connected to the electrodes and a voltage regulator for regulating the voltage on the at least one first electrode and the at least one second electrode in order to generate the electric field, said at least one first electrode being insulated from the interior of the receiving member by said dielectric.

Advantageously, the at least first electrode is covered by the dielectric. In the concext of the invention, dielectric means a substance or material which does not possess free electrons capable of carrying an electric current, but which may be polarised by an electric field. The dielectric is positioned so as to isolate the at least one first electrode from the stent and the second electrode, thus enabling an electric field to be generated when a voltage is applied to the first electrode (the second electrode being connected to earth). The dielectric may be made of any insulating material. For example, the dielectric may be made of PVC, parylene, glass, Teflon, ceramic, epoxy resin, Kapton or polymethacrylate. In some cases, the dielectric may be the original microcatheter in which the stent graft is stored prior to implantation. The dielectric may be between 10 µm and 10 mm thick. When the stent is positioned in the device, the thickness of the dielectric is defined as the distance between the metal part of the electrode and the stent, with the different elements in contact.

Advantageously, the voltage for generating an electric field may also be applied in the second electrode, the first electrode being connected to earth in this configuration. The stent, if it is metallic, may also be used as an electrode.

Advantageously, the receiving element may be any support allowing the vascular stent to be maintained during the process and, in particular, the original microcatheter. It is tubular in shape and may be, for example, a PVC tube (or any of the dielectrics mentioned as an example above) into which the vascular stent is introduced.

Figure 1A:
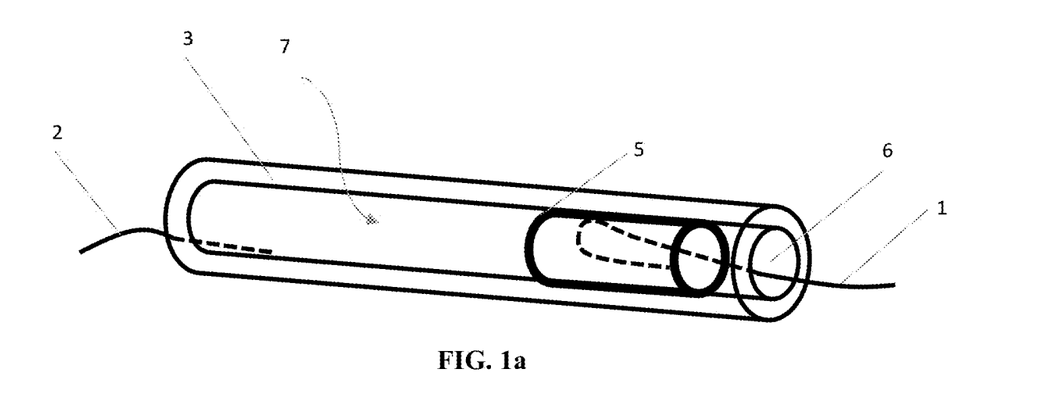
FIGS. 1a and 1b represent a device according to the invention in which the receiving element and the dielectric are different and comprising a vascular stent.
Figure 1B:
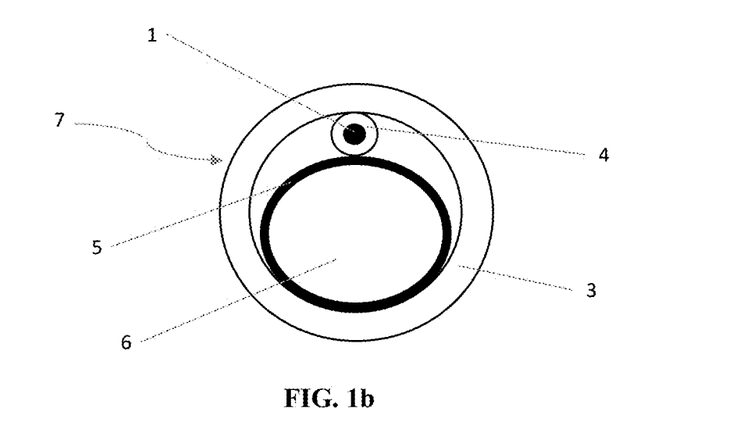

FIGS. 1a and 1b represent a device 7 according to the invention in which a deployed stent 5 is positioned. The first electrode 1 covered by the dielectric 4 is positioned between the receiving element 3 (which may be insulating) and the stent 5 (see FIG. 1b in cross-section). The second electrode 2 is located inside the receiving element 3 at a distance of 5 to 15 cm, preferably 8 to 12 cm and even more preferably 10 cm from the stent. The aqueous solution containing at least one protein is intended to circulate in cavity 6 of the receiving element 3. The generation of the pulsed electric field between the two electrodes leads to the formation of the film of at least one protein on the surface of the stent which is in direct contact with the aqueous solution.

Advantageously, the receiving element and the dielectric may be the same or different. For example, the dielectric may be a PVC tube in which the stent will be placed during the procedure (see FIG. 2). In this configuration, the thickness of the dielectric corresponds to the thickness of the receiving element, which may be a PVC tube (or any of the dielectrics shown in the example above).

Figure 2:
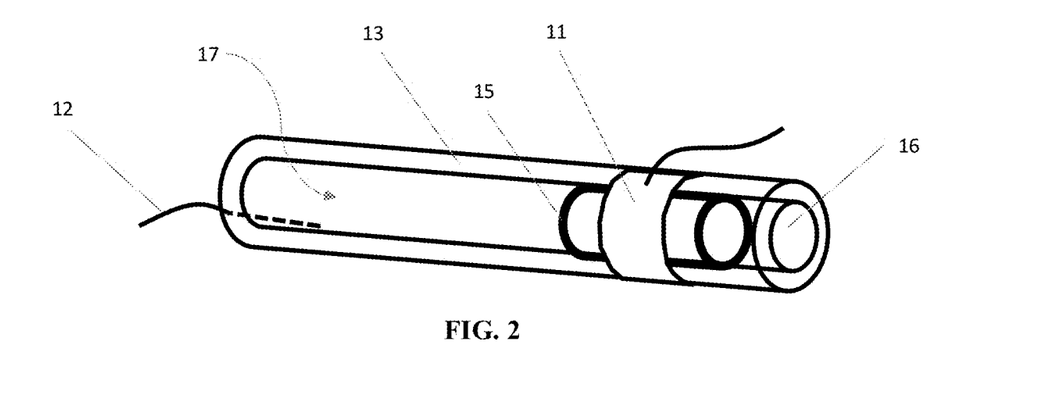
FIG. 2 represents a device according to the invention in which the receiving element and the dielectric are identical and comprising a vascular stent.

FIG. 2 represents a device 17 according to the invention in which a stent 15, deployed or non-deployed, is positioned. The first electrode 11 is located on the outer surface of the receiving element 13 which acts as a dielectric in this configuration. The second electrode 12 is located inside the receiving element 13 at a distance from the stent in the range of 5 to 15 cm, preferably 8 to 12 cm and even more preferably 8 cm. The aqueous solution comprising at least one protein is intended to circulate in cavity 16 of the receiving element 13. The generation of the pulsed electric field between the two electrodes leads to the formation of the film of at least one protein on the surface of the stent which is in contact with the aqueous solution. In this configuration, the first electrode may be a so-called ring electrode or a plurality of electrodes positioned on the external surface of the receiving element. The second electrode may be a single grounded wire or an annular electrode positioned inside or outside the receiving element 13.

Advantageously, the receiving element may be the original microcatheter of the stent. In this example, the procedure is performed on an undeployed stent.

Advantageously, when the stent has intrinsic, partial or total dielectric properties or comprises one or more dielectric material(s), the process according to the invention may be implemented directly by positioning the system of electrodes on the vascular stent. The vascular stent is brought into contact with the aqueous solution comprising at least one protein. In this configuration, the stent acts as a dielectric. The electric field applied by the system of electrodes is made possible by the insulating properties of the stent.

Advantageously, when the stent is metallic, it may be used as a grounded or energised electrode. In this configuration, electrode 2 or 12 may no longer be required.

Advantageously, the ends of the receiving element may be closed during the process, the aqueous solution comprising at least one protein is then immobile or stagnant during the process.

The invention also relates to a kit comprising a device according to the invention, an aqueous solution comprising at least one protein as defined above and possibly a vascular stent.

The invention further relates to a use of the device or kit according to the invention for coating vascular stents with a film of at least one protein of interest.

Other advantages may also appear to the skilled tradesman when reading the examples below, illustrated by the attached figures, which are given for illustrative purposes only and are not exhaustive.

BRIEF DESCRIPTION OF THE FIGURES

FIGS. 3c and 3d show the surface condition of the untreated stent C and the treated stent A, respectively.

EXAMPLES

Example 1a: Preparation of a Vascular Stent According to the Invention (Stent A)

A first high-voltage electrode is inserted into a PVC tube, which is a conductive wire covered with a dielectric (this electrode is a micro-guide used in neurosurgery). The metal core of the electrode has a diameter of 170 μm and is covered with a 50 μm thickness of parylene (dielectric) (this leads to a total external diameter of the microguide of 270 μm).

A nitinol flow diverter stent (Silk registered trademark) is deployed in the transparent PVC tube with an internal diameter of 3.7 mm and an external diameter of 6 mm. The inner wall of the PVC tube is heparinised, i.e. it is incubated with heparin, a powerful anticoagulant (it prevents the formation of fibrin) that will cover the entire surface of the PVC tube and prevent the activation of circulating cells that could mask the effect of the stent treatment.

The first electrode (micro-guide) is held between the stent and the inner wall of the PVC tube. The length of the PVC tube is 20 cm. The length of the expanded stent is about 4 cm and one end of the stent is about 2 cm from one end of the PVC tube.

At the other end of the PVC pipe, a lead wire (second ground electrode) is placed in the PVC pipe. The distance between the conductor wire and the stent is about 10 cm. The PVC tube is filled with blood plasma (or PBS containing albumin) and both ends of the PVC tube are clamped to prevent the plasma from flowing out.

The wire ends of the first and second electrodes remain accessible on the outside of the PVC pipe over a length of several centimetres.

The end of the conductor wire is connected to ground and the metal core of the high-voltage electrode is connected to a voltage supply.

Positive voltage pulses with an amplitude of 10 kV and a duration of 500 ns at a frequency of 100 Hz are applied for 20 minutes.

The treated stent A is obtained.

Example 1b: Preparation of a Vascular Stent According to the Invention (Stent B)

The nitinol flow diverter stent (Silk+ registered trademark: Blat Extrusion Monmorency, France) is placed in a transparent PVC tube with an internal diameter of 1.6 mm and an external diameter of 2.4 mm. The length of the PVC tube is 20 cm. The length of the deployed stent is approximately 2.5 cm and one of its ends is at a distance of approximately 2 cm from one of the edges of the PVC tube.

The outer surface of the PVC tube is wrapped with a metal electrode (copper tape) about 1 cm wide. The width of the tape partly covers the stent, which is separated from the conductive electrode by the dielectric thickness of the PVC tube. At the other end of the PVC tube, a conductive wire is placed in the PVC tube. The distance between the conductive wire and the stent is about 8 cm.

The PVC tube is filled with blood plasma (or PBS containing albumin) and both ends of the PVC tube are clamped to prevent the plasma from flowing out. The end of the conductor wire is accessible outside the PVC tube for a length of several cm.

The end of the conductor wire is connected to ground and the outer electrode (the metal tape) to a voltage supply.

Positive voltage pulses with an amplitude of 10 kV and a duration of 500 ns at a frequency of 100 Hz are applied for 20 min.

Stent B is Obtained.

In the following, stent C will refer to a control stent, untreated, not being part of the invention.

Example 2: Results

Figure 3:
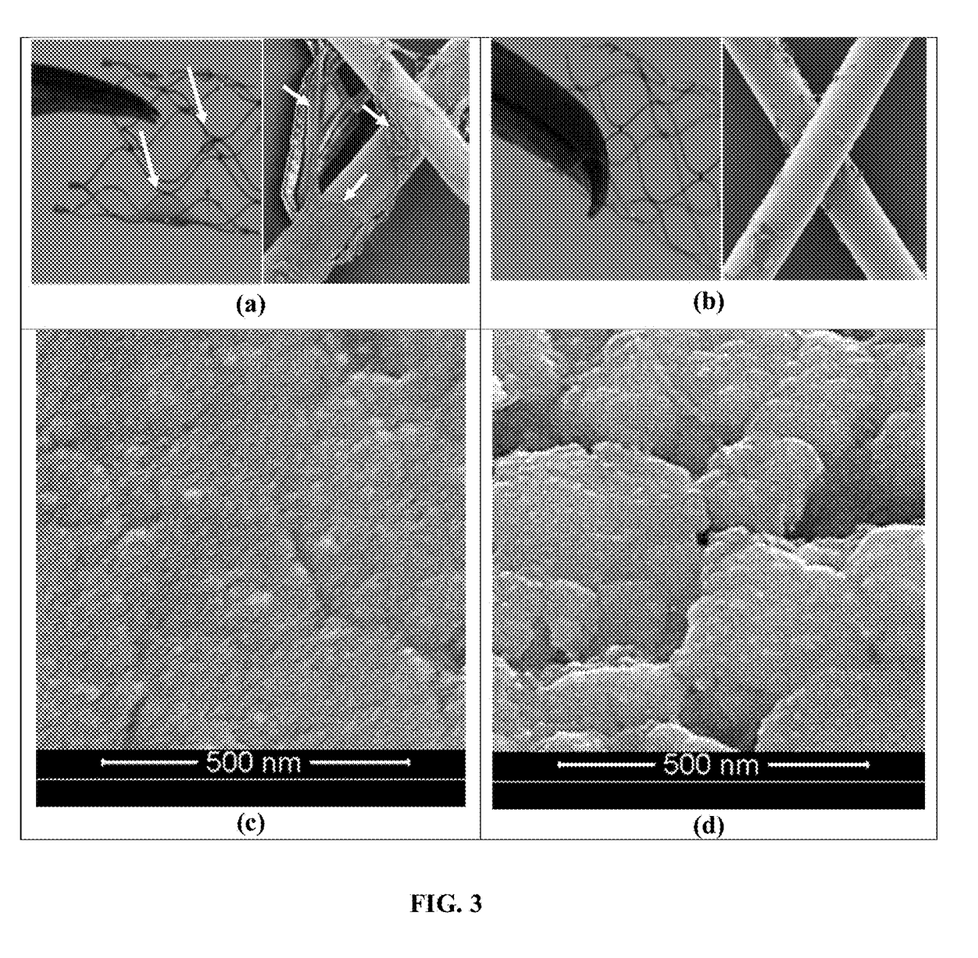
FIG. 3 represents a comparison of the visual and scanning electron microscopy (SEM) appearance of (a) stent C, untreated after its extraction from the PVC tube and (b) stent A, treated according to the invention, 14 days after its treatment.

After treatment, the plasma in contact with the stent A, treated according to the invention, of example 1a is replaced by human blood (it is poured into the same PVC tubing used for the treatment). The assembly is then placed in a Chandler Loop System® device (industriedesign, ebo kunze) to reproduce the rheological conditions of circulation in a blood vessel (the PVC tube in the form of a torus is rotated in a water bath at 37° C. so that the blood is set in motion in the tube as it would be in an artery). An untreated stent C is prepared under the same operating conditions but without being subjected to the electric field. After 1 hour of rotation in the Chandler Loop, the stents A or C are removed from the PVC tube. Blood is collected for analysis and platelet count. FIG. 3 (a) shows the visual and scanning electron microscopy (SEM) appearance of the untreated stent C after removal from the PVC tube. The surface of the stent (see white arrows) is the site of platelet thrombus formation and fibrin threads are visible between the stent mesh. FIG. 3 (b) shows the appearance of stent A, treated according to the invention, 14 days after treatment. No platelet thrombi or fibrin filaments are observed in the same pattern. FIG. 3 (b) thus shows that the effects persist at least 14 days after treatment of the stent.

The various tests carried out show that the effect lasts at least up to 6 months.

Thus, when the stent is simply brought into contact with human plasma (without the application of the electric field), a thick deposit of protein is observed which fills the nitinol asperities (FIG. 3 (c)), whereas the film of protein(s) induced by the application of the electric field is much thinner (FIG. 3 (d)). The scales of the nitinol alloy on the surface of the stent A are still visible, whereas they are no longer visible on the untreated stent C.

Figure 4:
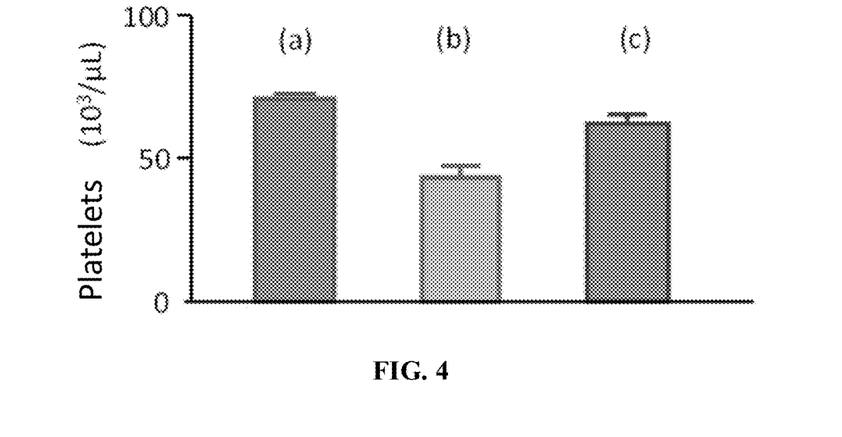
FIG. 4 represents the impact on the platelet count of the blood after passing through the Chandler Loop with stent A or C as described in Example 2. (a) Blood extracted from the tubing after passage through the Chandler Loop and in the absence of a stent; (b) Blood extracted from the tubing after passage through the Chandler Loop and in the presence of a stent C, untreated; (c) Blood extracted from the tubing after passage through the Chandler Loop and in the presence of a stent A, according to the invention.

FIG. 4 shows that stent A, treated according to the invention, has an impact on platelet blood counts. In the three cases presented (a), (b) and (c), the platelet count in the blood is measured after 1 hour of rotation in the Chandler Loop. It can be seen that the level of platelets in the blood is lowered in the case of stent C, untreated, as a result of their interaction with the stent (FIG. 4b), whereas in the presence of stent A, treated according to the invention (FIG. 4c), the level of free platelets observed in the absence of a vascular stent (FIG. 4a) is found.

Figure 5:
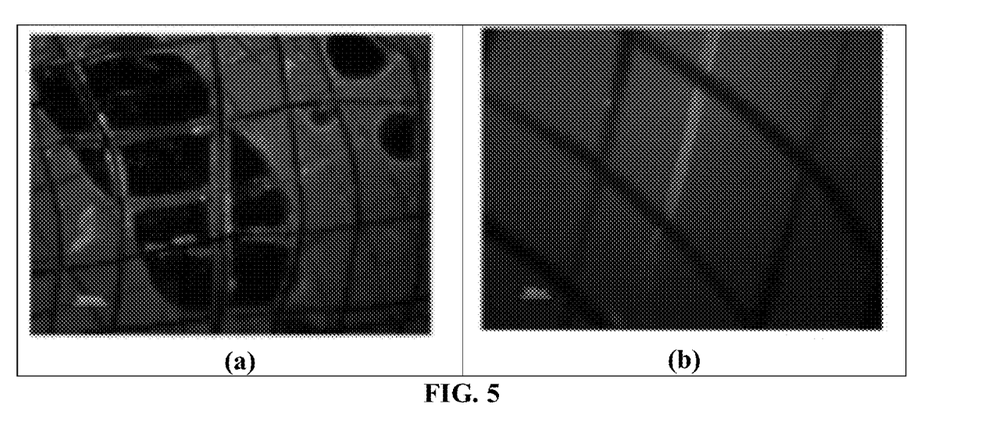
FIG. 5 represents (a) the surface of an untreated stent C and (b) the surface of a stent A, according to the invention, observed in the focal plane of a fluorescent epi-microscope after protein labeling with an Alexa 488 NHS probe.
Figure 6:
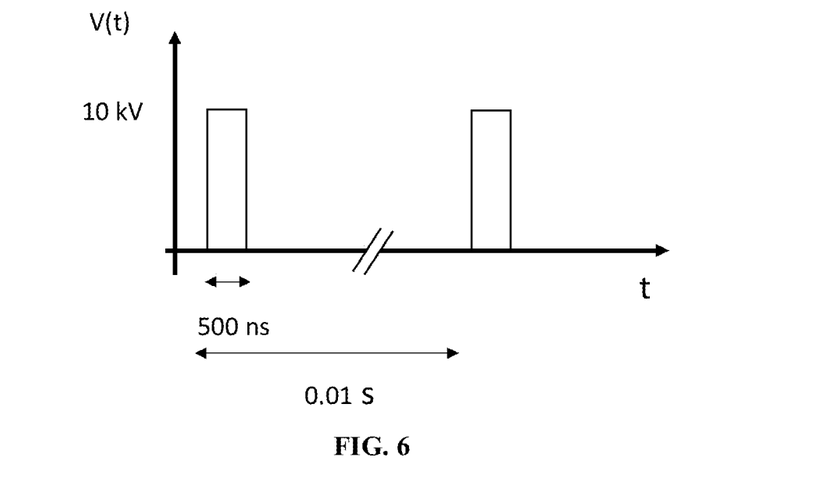
FIG. 6 represents an example of an electrical signal (voltage in volts as a function of time in seconds) that can be applied to the system of electrodes of the device according to the invention, allowing the electric field to be generated according to the process of the invention.

The blood proteins were labelled using a probe (NHS Alexa 488) which binds covalently to the terminal —NH2 part of the proteins. This enables the proteins to be visualised by fluorescent spike microscopy. FIG. 5 shows a comparison between an untreated stent which has been in contact with human blood and stent A, treated according to the invention, which has been in contact with human blood for a period of 2 hours in the Chandler Loop. The untreated stent C in FIG. 5 (a) shows a high and relatively heterogeneous fluorescence in the focal plane of the microscope due to platelet adhesion and the fibrin network being formed (thrombosis). The stent treated according to Example 1 shown in FIG. 5 (b) exhibits homogeneous fluorescence in the focal plane of the microscope only on the surface of the stent (homogeneous thickness) indicating the presence of the film of at least one protein present on the surface of the stent A treated according to the invention.

Example 3: Identification and Quantification of Proteins Deposited on the Stent

The stent was subjected to different treatment conditions (untreated and treated according to the invention), then incubated in 300 μl of laemmli buffer (4% SDS, 10% DTT, 20% glycerol, 0.004% bromophenol blue, 0.125 M TRIS HCL; pH=6.8) for 10 minutes at 90° C. and then 1 min with stirring. The stents are recovered and then soaked again in the same volume of laemmli buffer but this time they are sonicated by an ultrasound cycle for 40 seconds at a frequency of 40 kHz. A 40 μl volume of the suspension is then analysed by SDS PAGE electrophoresis.

Figure 7:
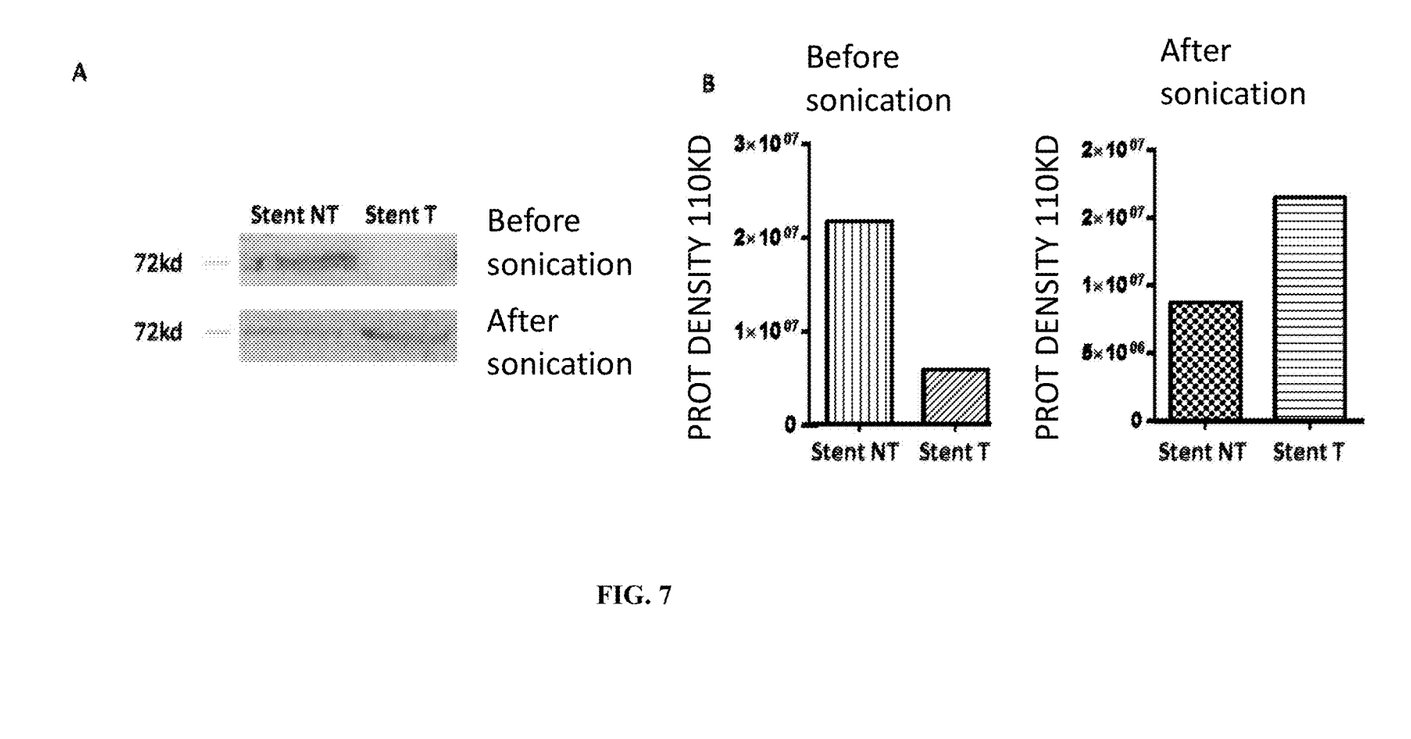
FIG. 7 (A) represents a comparison of the proteins released by a stent A, treated according to the invention (T) or C, untreated (NT), after chemical treatment and before/after sonication and analysed by SDS PAGE electrophoresis. (B) represents the quantification by densitometry of the protein bands separated by SDS PAGE electrophoresis.

After migration, the proteins will be revealed for Imperial stain (BIORAD) and the area corresponding to albumin (majority protein observed) is shown in FIG. 7A.

Unlike the untreated (NT) stent, the treated (T) stent requires a sonication step so that the deposited protein film can be retrieved and analysed, as shown in FIGS. 7A and 7B. This result demonstrates that the protein film deposited during processing of the treated stent is very strongly adhered to the surface of the stent which correlates with the observation of the persistence of the effect of the stent treatment over a long period of time (6 months at 4° C.).

Example 4: Endothelialization Test in Static Cell Culture

Figure 8:
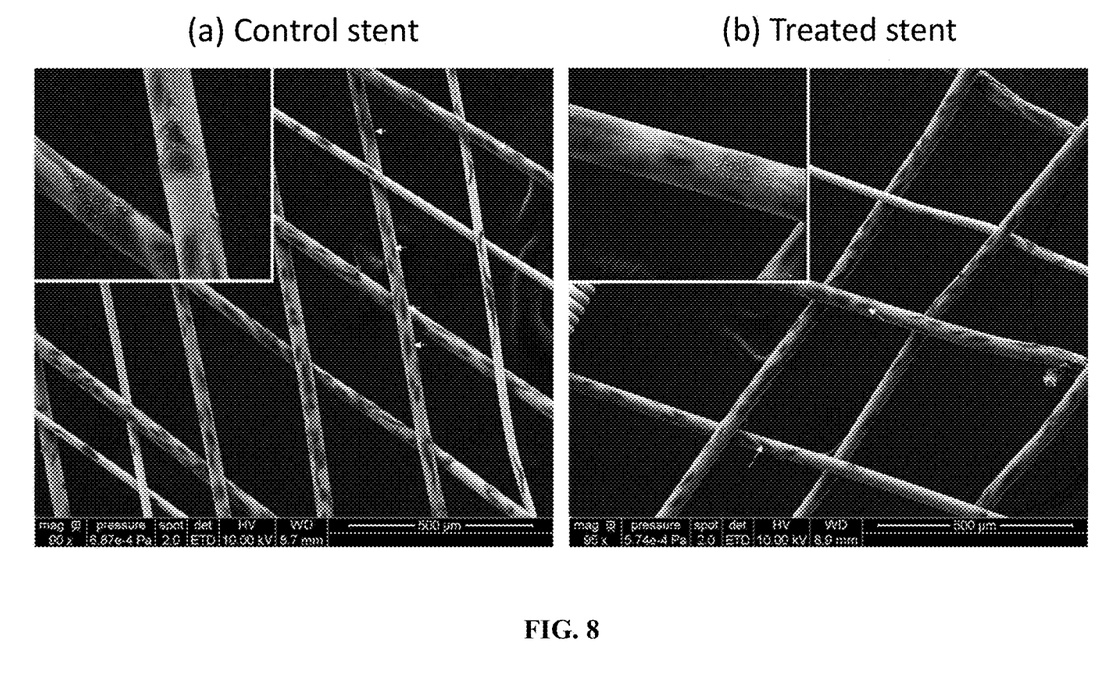
FIG. 8 represents a scanning electron microscopy image showing the colonization by human endothelial cells (HUVEC) of an untreated (control) stent C (a) and a treated stent A according to the invention (b) after 5 days of static culture. Magnification of 90× and 500× for the zoom window. (Scale: 500 μm).

After treatment with the electric field, the stent A, treated according to the invention, was removed from the PVC tube and placed for 5 days in a culture medium containing human endothelial cells (HUVEC) in suspension. Scanning electron microscopy images of the stent show that the treatment does not prevent the endothelial cells from colonizing the surface of the stent under static conditions. The black spots observed in FIGS. 8 (*a* and *b*) correspond to adhered endothelial cells (some of which are indicated by arrows). The images in FIG. 8 clearly show that the endothelial cells adhere to the surface and that the coverage rate at 5 days is the same for an untreated stent C (a) as for a stent A treated according to the invention (b).

Example 5: Effect of Treatment on Leukocyte Recruitment

Figure 9:
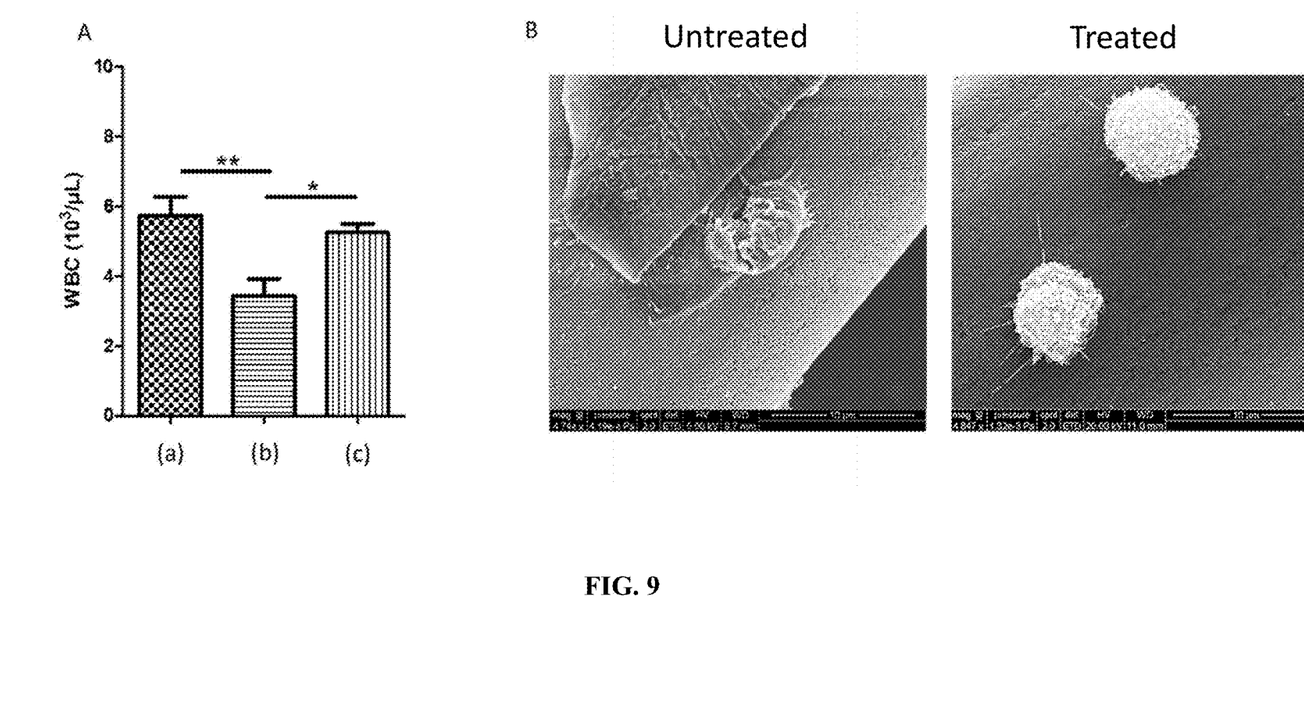
FIG. 9 shows a comparison of leukocyte adhesion on an untreated stent and a stent treated according to the invention after 1 hour rotation of a control blood in the Chandler Loop. (A) represents the amount of free white blood cells in the blood after the Chandler Loop, (B) is a scanning microscopy image showing the appearance of white blood cells interacting with the surface of an untreated stent C (left) or A treated according to the invention (right). Magnification 4700×. (Scale: 10 μm).

It can be seen that the treatment of the stent according to the invention also has an impact on the recruitment of circulating leukocytes after 1 hour of rotation in the Chandler Loop, as shown in FIG. 9A. When the stent is untreated, the white blood cell count after 1 hour of rotation is lowered, which is not the case when the stent is treated. In addition, observation with a scanning electron microscope (FIG. 9B) shows that the white blood cells are very spread out on the untreated stent (a sign of strong adhesion and cell activation). On the contrary, the rare leukocytes that interact with the stent treated according to the invention keep their rounded shape (their attachment to the surface of the stent is therefore fragile).

This result demonstrates a beneficial impact of stent treatment on the recruitment and activation processes of leukocytes, which can reduce the inflammation generally observed during stent placement.

LIST OF REFERENCES

[1] WO2017/004598

The invention claimed is:

1. Vascular stent, deployed or non-deployed, comprising a surface coated by a film comprising at least one protein which has been subjected to an electric field generated by a system of electrodes comprising at least one first electrode, a dielectric and at least one second electrode, said dielectric electrically isolating the stent and the at least one second electrode from the at least one first electrode;
wherein the electric field is generated by a voltage signal applied to the system of electrodes having an amplitude ranging from 0.1 kV to 50 kV, having a duty cycle ranging from $5 \times 10^{-8}$ to 1, and having a frequency ranging from 0.1 Hz to 100 kHz.

2. A vascular stent according to claim 1, wherein the at least one protein comprises at least one of blood plasma proteins, a synthetic biological macromolecule, and mixtures thereof.

3. A vascular stent according to claim 1, wherein a concentration of the protein on the surface of the stent is greater than or equal to 2 µg/cm$^2$.

4. A stent according to claim 1, wherein the stent comprises one or more alloys selected from the group consisting of stainless steel, nickel/titanium, tantalum, cobalt/chromium, platinum/chromium alloys, alloys optionally including magnesium, and mixtures thereof.

5. A process of coating a surface of a vascular stent, deployed or non-deployed, with a film of at least one protein, comprising the steps of:
bringing the vascular stent into contact with an aqueous solution comprising the protein,
application of an electric field generated by a system of electrodes comprising at least one first electrode, a dielectric and at least one second electrode, said dielectric electrically isolating the stent and the at least one second electrode from the at least one first electrode,
wherein the electric field is generated by a voltage signal applied to the system of electrodes having an amplitude ranging from 0.1 kV to 50 kV, having a duty cycle ranging from $5 \times 10^{-8}$ to 1, and having a frequency ranging from 0.1 Hz to 100 kHz, and
coating of the surface of the stent with the film of the protein.

6. A process according to claim 5, wherein the concentration of the protein in the aqueous solution is greater than or equal to 0.1 mg/ml.

7. A process according to claim 5, wherein the protein comprises at least one of blood plasma proteins, a synthetic biological macromolecule, and mixtures thereof.

8. A process according to claim 5, wherein the electric field is applied for a duration greater than or equal to 10 seconds.

9. A device for carrying out the process according to claim 5, comprising:
at least one first electrode,
at least one second electrode,
at least one dielectric isolating the first electrode from the second electrode,
a receiving element capable of containing the vascular stent, said receiving element being identical or different from the dielectric.

10. A vascular stent according to claim 2, wherein the at least one protein comprises albumin.

11. A process according to claim 5, wherein the amplitude of the voltage signal ranges from 5 kV to 40 kV.

12. A process according to claim 5, wherein the voltage signal has a duty cycle ranging from $5 \cdot 10^{-6}$ to $5 \cdot 10^{-3}$.

13. A process according to claim 5, wherein the voltage signal has a frequency ranging from 1 Hz to 1 kHz.

14. A process according to claim 5, wherein the electric field is applied for a duration greater than or equal to 5 minutes.

15. A kit comprising:
the device of claim 9;
an aqueous solution comprising a protein; and
a vascular stent;
wherein the protein comprises at least one of a blood plasma protein, a synthetic biological macromolecule, and mixtures thereof.

* * * * *